Figure 1:
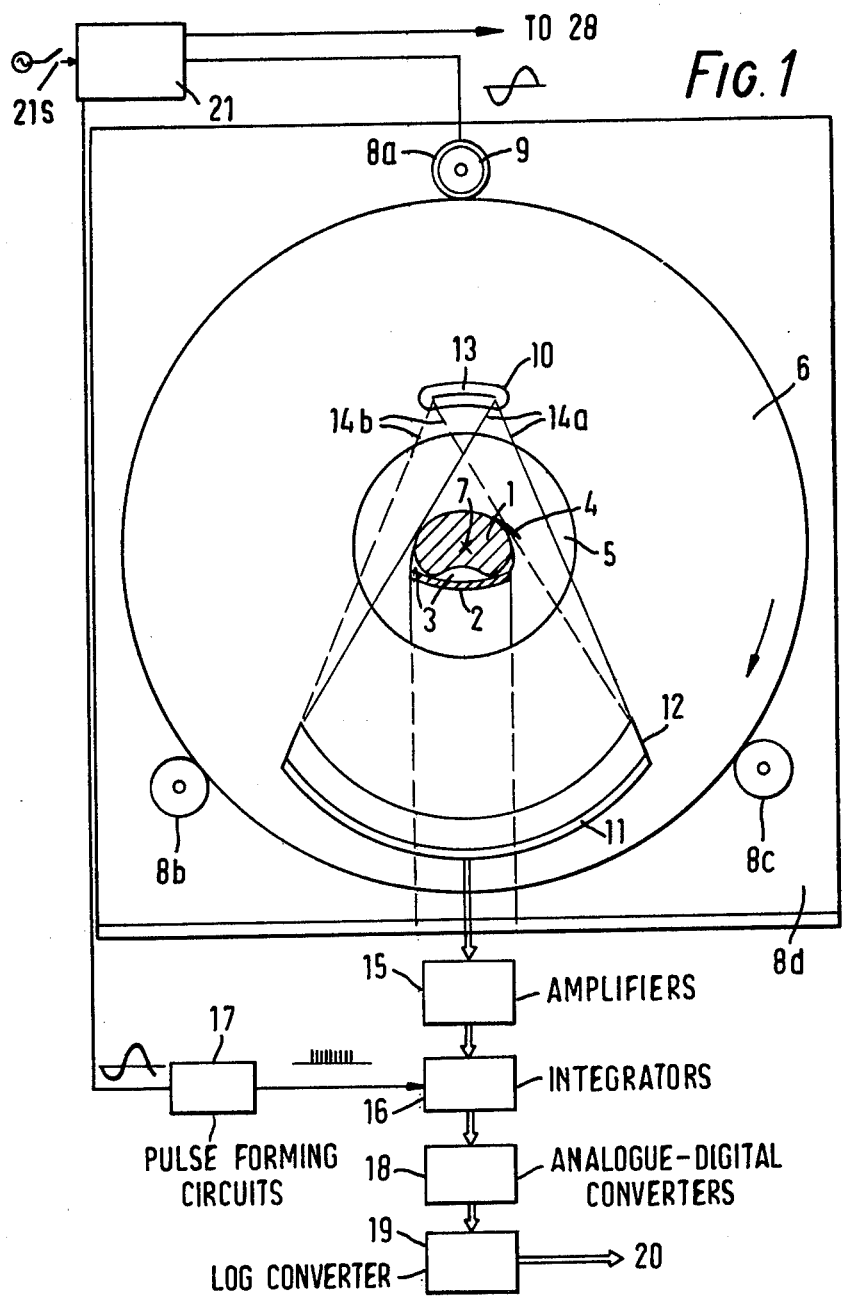

United States Patent [19]
LeMay

[11] 4,097,744
[45] * Jun. 27, 1978

[54] RADIOGRAPHIC APPARATUS HAVING REPETITIVE MOVEMENT OF THE ORIGIN OF THE RADIATION

[75] Inventor: Christopher Archibald Gordon LeMay, Osterley, England

[73] Assignee: EMI Limited, Hayes, England

[*] Notice: The portion of the term of this patent subsequent to Mar. 1, 1994, has been disclaimed.

[21] Appl. No.: 725,507

[22] Filed: Sep. 22, 1976

Related U.S. Application Data

[63] Continuation of Ser. No. 630,779, Nov. 11, 1975, Pat. No. 4,010,370.

[30] Foreign Application Priority Data

Nov. 13, 1974 United Kingdom ............... 49074/74

[51] Int. Cl.² ..................... G01N 21/34; G01N 23/04; G01T 1/20
[52] U.S. Cl. .................... 250/366; 250/402; 250/445 T
[58] Field of Search .................. 250/402, 445 T, 366, 250/369

[56] References Cited

U.S. PATENT DOCUMENTS 4,010,370  3/1977  LeMay ................................. 250/366

Primary Examiner—Alfred E. Smith
Assistant Examiner—T. N. Grigsby
Attorney, Agent, or Firm—Cooper, Dunham, Clark, Griffin & Moran

[57] ABSTRACT

Radiographic apparatus is provided to evaluate the absorption coefficient of a body at each of a plurality of locations distributed over a cross-sectional slice of the body of a patient. A source directs a fan-shaped distribution of radiation through the slice and is orbited to direct the radiation from a plurality of directions. Detectors are provided to detect the radiation emergent from the body along a plurality of paths. A lateral can, which may be along a curved path, is superimposed on the source motion. This is arranged so that over a predetermined time period, it substantially cancels the orbital motion to effect a part of a lateral scan and give some parallel paths through the body. Over several time periods there can be erected a full set of beam paths which not only partly overlap to give comparison of detector sensitivities but also provide the parallel set which although not essential is useful for the convolution processing.

28 Claims, 7 Drawing Figures

RADIOGRAPHIC APPARATUS HAVING REPETITIVE MOVEMENT OF THE ORIGIN OF THE RADIATION

This is a continuation of Application Ser. No. 630,779, filed Nov. 11, 1975 Now U.S. Pat. No. 4,010,370.

This invention relates to a method of and apparatus for constructing a representation of the variation of absorption of a planar slice of a body with respect to penetrating radiation such as X- or γ-radiation.

One method of and apparatus for constructing such a representation is described in U.S. Patent Ser. No. 3,778,614. According to one example given in that specification a scanning movement is imparted to a suitable source of radiation to provide a plurality of substantially parallel pencil beams of radiation at each of a plurality of inclinations in the plane of the slice. A suitable detector is scanned in a corresponding manner to provide a measure of the absorption suffered by each of the beams in passing through the body. These measurements of absorption are then processed by suitable means to provide a distribution of linear absorption coefficients for the planar slice. To provide the required plurality of beams the source and detector are reciprocated in the plane of the slice and orbited in steps about a common axis normal to that plane.

An alternative processing method involving a form of convolution is further described in U.S. Pat. No. 3,924,129.

In our co-pending U.S. Pat. No. 3,946,234 there is described a variation of the apparatus of the said British Patent, for the same purpose, having a source arranged to produce a fan shaped beam of radiation having a wide angular spread in the plane of examination. Collimators are provided to divide that beam into a plurality of pencil beams and an array of detectors is provided to detect the intensity of each of those pencil beams after passage through the body. Scanning motions as described are further imposed on the source-detector unit. As a result of the lateral scanning movement the array of detectors provides absorption information for a plurality of sets of parallel beams of radiation, the sets being angularly spaced by the angular separation of the beams. Thus the orbital step between each lateral movement is through a relatively larger scale. That variation of the apparatus is therefore capable of providing a faster scanning movement than that of the said British Patent. However for the examination of certain parts of the body it is desirable to further increase the scanning rate.

To that effect our co-pending U.S. Pat. No. 3,937,963 describes a method of and apparatus for constructing the said representation in which the angular spread of the fan shaped beam is sufficient to include the whole region of interest in the plane of the body so that a complete scan can be effected solely by orbiting the source and detectors about the common axis.

For both of the arrangements of the said U.S. Pat. Nos. 3,937,963 and 3,946,234 it is preferable for the orbital motion to be continuous rather than being stepped and occurring between determination of absorption. Unfortunately, however, such continuous motion results in data being obtained for beam paths which are distorted, as a result of motion in the course of a detector reading, and, in the case of the arrangement of U.S. Pat. No. 3,946,234, for sets of beam paths obtained in the course of a lateral scan which are not parallel as is desired but are distributed in the form of a fan.

It is an object of this invention to provide an improved arrangement allowing continuous orbital movement for the scanning methods of both of said applications.

It is another object of the invention to provide an arrangement which, with a continuous orbital movement allows convenient comparison of detector outputs for calibration of sensitivities.

It is a further object of the invention to provide a radiographic apparatus in which the source is angularly displaced and the beams of radiation are subject to an additional displacement which maintains each of the beams parallel to its initial position to examine some paths examined previously by another detector to give a single absorption value despite differences in detector sensitivities.

It is yet another object of the invention to provide a radiographic apparatus in which the radiation source is angularly displaced and subject also to a further displacement to keep each beam for a time parallel to its initial position so that some absorption values are given by combinations of output signals for more than one path.

It is a further object of the invention to provide a radiograhic apparatus in which the source of the radiation is subject to an angular displacement and a repetitive additional displacement to examine paths in a different linear zone of the body for each repetition wherein each zone overlaps, at least in part, at least one other zone.

It is another object of the invention to provide a radiographic apparatus in which a source of a fan-shaped swath of radiation is angularly displaced and subject to a further displacement to irradiate several series of parallel paths each series examined by a different detector, in which a detector output for one series of such paths is combined with outputs from other detectors obtained at different times for other series to provide data for a larger group of parallel paths distributed across a region of interest in the body.

It is another object of the invention to provide a radiographic apparatus in which a source of a fan of radiation is angularly moved, about the body, on a support and in which beams in the fan are further repetitively displaced such that they remain at the same inclination relative to the body throughout each repetition.

It is yet another object of the invention to provide a radiographic apparatus employing a fan-shaped distribution of radiation, in which relative movement is provided between the distribution and the detectors so that a detector views the origin of the radiation in different positions and receives radiation along different paths originating at those positions.

Figure 2:
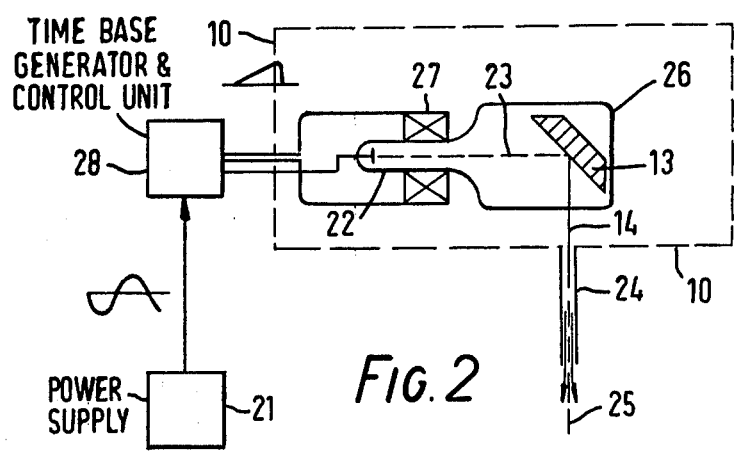
Figure 4:
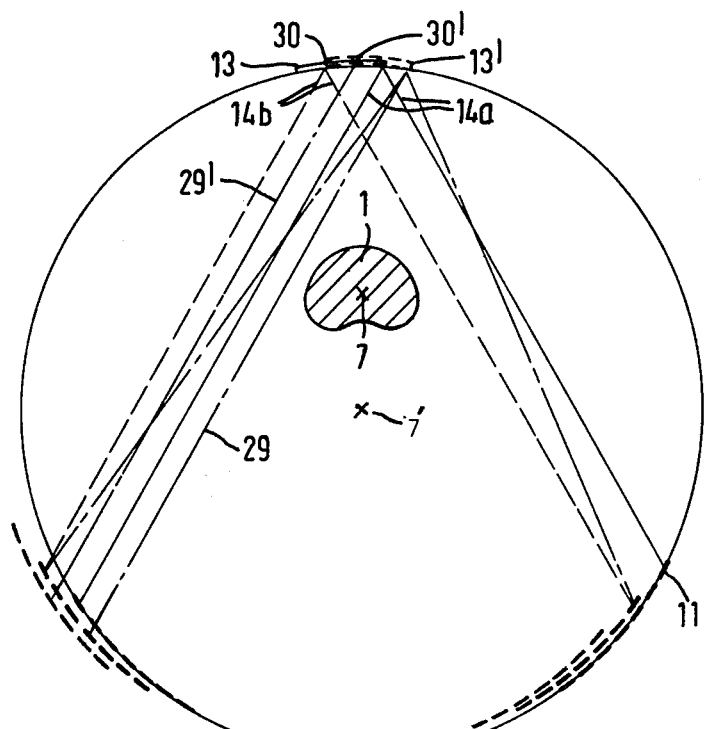
Figure 3:
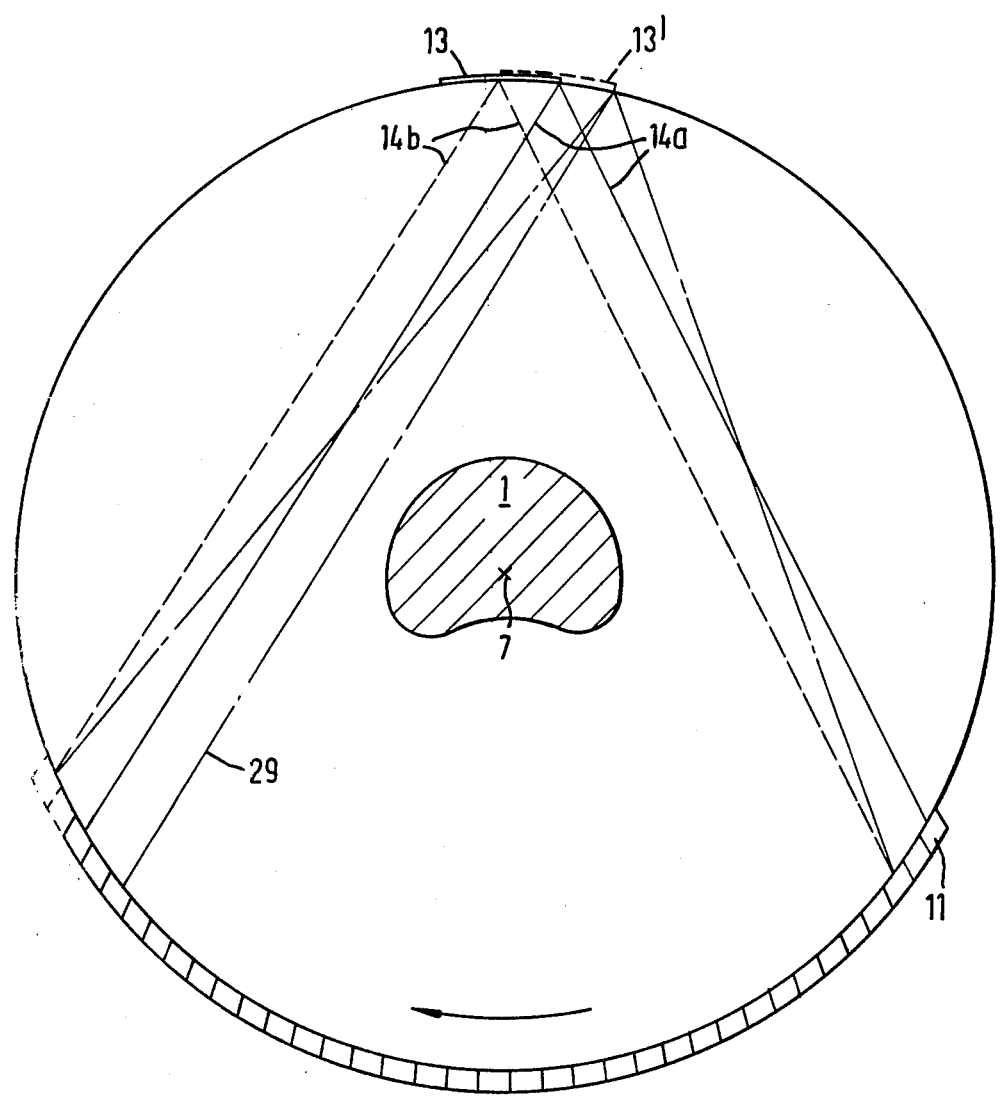
Figure 5:
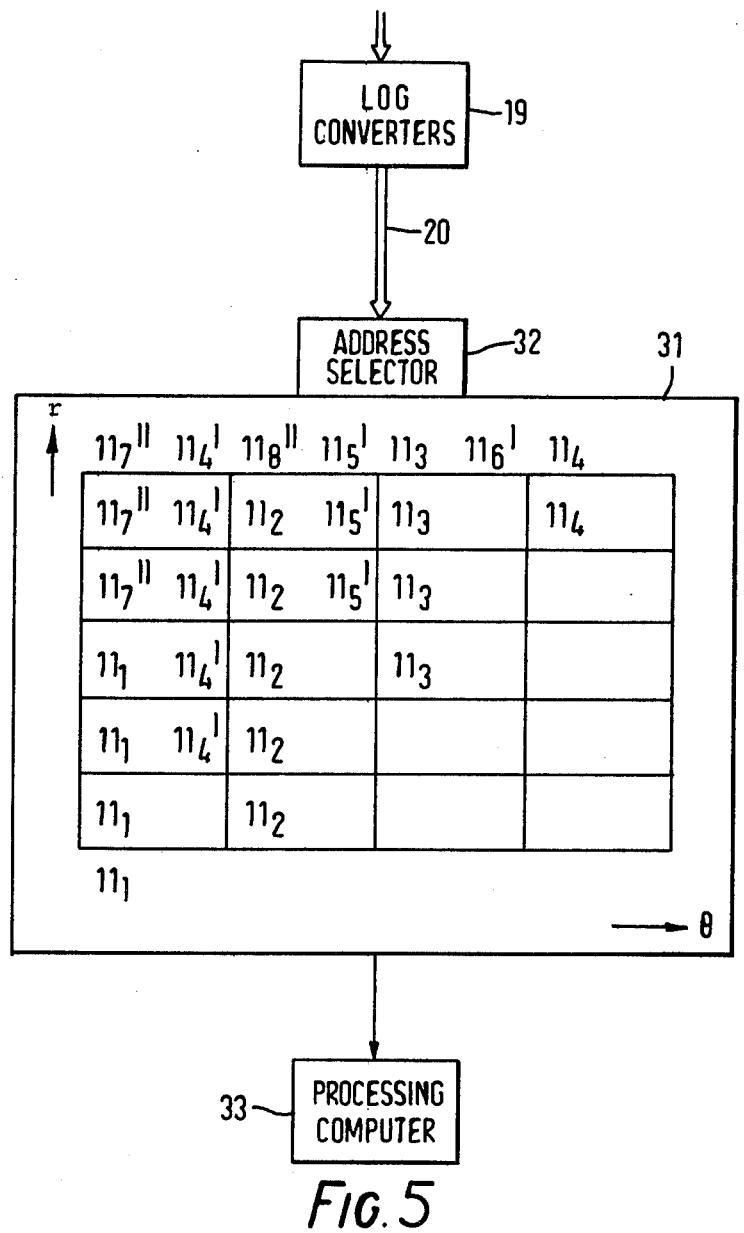
Figure 6:
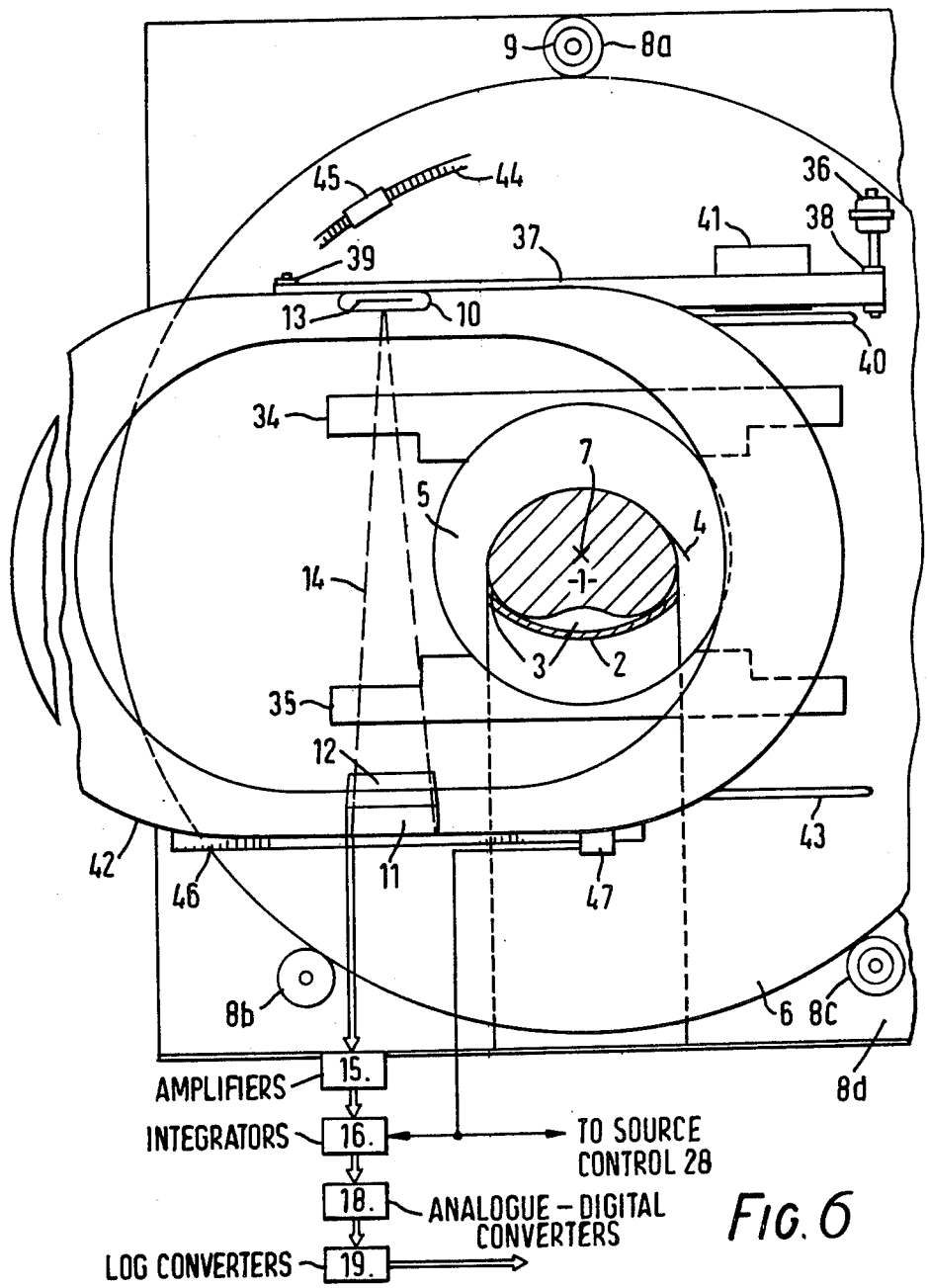
Figure 7:
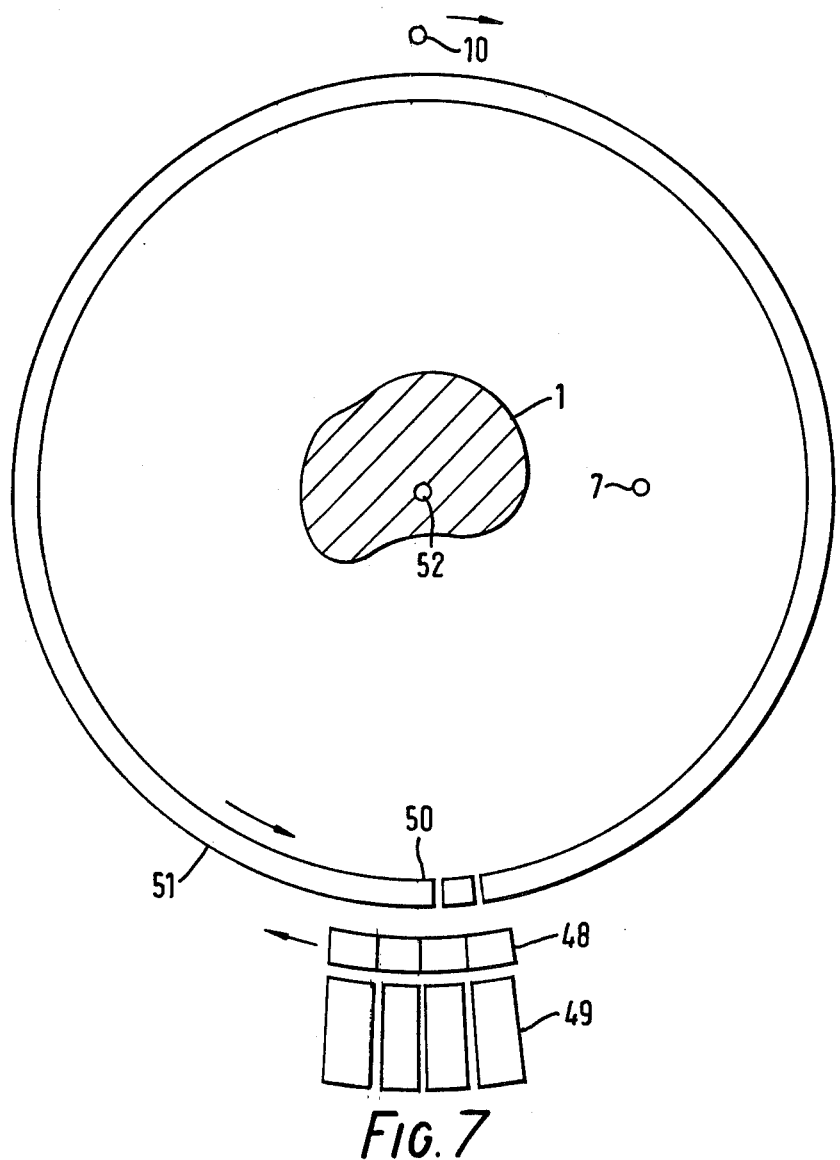

In order that the invention may be clearly understood and readily carried into effect examples will now be described with reference to the accompanying drawings of which:

FIG. 1 shows one example of an X-ray apparatus incorporating an embodiment of the invention, FIG. 2 shows an X-ray source suitable for use with the invention, FIG. 3 illustrates the scanning movements of one example of the invention, FIG. 4 illustrates the scanning movements of another example of the invention, FIG. 5 is a diagram used to explain the organisation of data derived from the example of FIG. 4, FIG. 6 shows another example of an X-ray apparatus incorporting an embodiment of the invention and FIG. 7 shows a simplified form of another embodiment of the invention.

Referring to FIG. 1 there is shown therein an apparatus, of the type described in the aforesaid U.S. Pat. No. 3,937,963 incorporating one example of the invention. A body 1 to be examined, shown in transverse section, is supported on a suitably shaped bed 2, also shown in transverse section. A material 3, having an absorption to the radiation similar to that of body tissue, is positioned between the body 1 and the bed 2, to substantially exclude air from the gap therebetween, and is extended partly about the body to provide an approximately circular cross-section to the radiation. The body is retained firmly in the desired position by means such as a retaining strap 4. If desired a more rigid retaining ring, such as the two part ring described in co-pending U.S. Pat. No. 3,937,963 may be used.

The bed 2 and the body 1 are inserted into an aperture 5 in a rotatable member 6 so that a desired part of the body is centred in the aperture. The rotatable member 6 is arranged to rotate about an axis 7, longitudinal of the body 1 and perpendicular to the paper, central to the aperture 5. For that purpose it is supported by three gear wheels 8 a,b,c, which engage with gear teeth, not shown, cut into the periphery of member 6. The gear wheels 8 are journalled in a main frame 8d of the apparatus which may take any form suitable to support the apparatus and to allow the necessary rotation. Gear wheel 8a is driven by a synchronous electric motor 9, also mounted on the main frame, the operation of which will be described hereinafter.

The rotatable member 6 also carries a source of X-rays 10, a bank of detectors 11 and associated collimators 12. The detectors, which in a typical embodiment number 200, can be of any suitable type, for example scintillation crystals with associated photomultipliers or photodiodes.

The source 10 is of the type which includes an elongated target/anode 13, which will be discussed further hereinafter, and provides a fan shaped spread 14 of X-rays from a substantially point origin in plan which can be scanned by electronic means from the position 14a to the position 14b shown. In this example the corresponding scan of the origin of the X-rays along target 13 is of the order of 10 cm although it may be less if desired. The collimators 12 have longitudinal axes which intersect at the centre of the anode 13, the axes being angularly spaced by about ⅓° from each other.

In this example the X-ray source 10 is placed of the order of 40cm from the central axis 7 with the detector 11 being placed a further 80cm. on the opposite side of axis 7 so as to intercept the radiation of fan 14 for any position of the point of origin of the X-rays in its lateral scan along target 13. The detectors and source preferably lie along arcs of a single circle which, in this example, is not concentric with axis 7. It should be understood that collimators 12 are of dimensions which allow such interception while preventing the reception of scattered reception to the greatest degree practically possible. Although in the example the distance between source 10 and axis 7 is half of that between detector 11 and axis 7, the relationship is for the purpose of obtaining a particularly beneficial result which will be explained hereinafter. If desired the source and detectors may be placed equidistant from the axis or in any other desired relationship.

Disregarding for the moment the rotary motion referred to hereinbefore, the arrangement is such that the point of origin of the X-rays is scanned steadily along target 13, taking the fan of X-rays from 14a to 14b, and is rapidly returned to the starting point before repeating the scan. During the time of one such scanning movement each detector of array 11 provides an output indicative of the intensity of radiation incident thereon. These outputs are amplified in amplifier 15 and then input to integrators 16. There the outputs are integrated over periods determined by a series of pulses from pulse forming circuits 17. In this example the timing of the pulses is such that there are eleven integration periods in the time of one lateral scan of X-ray fan 14 from 14a to 14b. Thus each detector measures radiation in effect along eleven narrow beams joining that detector with eleven equally spaced positions along target 13. Hereinafter the word beam will be used to denote a beam of radiation incident on a detector and scanned with the source and detectors.

Conversely the path through the body irradiated by a beam, and fixed in relation to the body, will be termed a beam path. The paths are, of course, of width determined by the integration intervals and are of a shape determined by the geometry of scanning movements in those intervals. For the purposes of illustration, however, they may be considered to be represented by single lines which are in fact their centre lines. The lines illustrating the extremes of fan 14 are in fact the centre lines of the extreme beams of the fan. Signals representing the intensity of radiation received along such paths are converted to digital form in converters 18 and to logarithmic form in converters 19 for output at 20 for further processing. It will be understood that one amplifier 15, integrator 16. A/D converter 18 and log converter 19 is provided for every detector, all operated in synchronism. The processing is effective to sort the signals into sets representing absorption along sets of parallel paths, as will be further explained hereinafter, for processing by a suitable method such as that described in our co-pending U.S. Pat. No. 3,924,129 to provide the desired representation. The circuits 15 to 19 are of well known construction.

In order to achieve the effect of the present invention, which will be described in detail hereinafter, motor 9 provides a continuous motion of rotable member 6 and all the equipment mounted thereon, in the direction shown by the arrow about axis 7 and therefore about the body 1 of the patient on bed 2. The rotary motion and the lateral scanning of X-ray fan 14 must be in a strict relationship to achieve the desired result. Synchronous motor 9 is driven by a periodic sinusoidal voltage from a power supply 21 and, after a suitable period of time, stablises in synchronisation with that sinusoidal voltage. It will be appreciated that, when under load, the motion of motor 9 lags the phase of the sinusoidal voltage but this is not significant provided the load does not change and therefore the lag is constant. The sinusoidal voltage from supply 21 is supplied to a time base generator 28 (FIG. 2) where it provides a periodic sawtooth waveform voltage, to operate the scanning of source 10, and also to unit 17 which converts it to square pulses of the same phase and generates therefrom the series of pulses, in strict phase relationship with the sinusoidal voltage, to clear and read integrators 16 as explained hereinbefore. Pulse forming circuit 17 operates in a conventional manner by any suitable means known in the art. Flyback of the sawtooth waveform takes place during selected resetting periods of the integrators.

The X-ray source 10 is shown in greater detail in FIG. 2 and in this example comprises an electron gun 22, powered by a conventional supply not shown, providing a beam of electrons 23 which is incident on target/anode 13 to provide X-ray fan 14. In FIG. 2 the elongation of target 13 is perpendicular to the paper so that the X-ray fan 14 is also perpendicular to the paper. Source collimator 24 is provided, as shown, to restrict the X-rays substantially to the plane of the fan, shown dotted at 25 and that is then the plane of a section of the body 1 to be examined. The electron gun and target are enclosed in an evacuated envelope 26 having a neck section around which are disposed scanning coils 27. In operation, a suitable time (to allow motor 9 to settle in speed) after power supply 21 is switched on by switch 21s in FIG. 1, the time base generator 28 is switched on by a delayed signal from power supply 21. This signal also switches on electron gun 22. The sawtooth voltage from generator 28 scans the point of incidence of the electron beam 23 along target 13 from one end in a direction perpendicular to the paper to scan the X-ray point as shown in FIG. 1. Although a pencil beam of electrons is indicated it will be understood that it may be a ribbon shaped beam used in conjunction with a suitable shape of target 13. Furthermore oil cooling of target 13, although not shown, is preferably provided in conventional manner. Although scanning coils have been shown in FIG. 2, deflection plates may be used if desired; any configuration of source 10 capable of achieving the scanning of the X-ray fan 14 being suitable for use with the invention. Alternatively any other suitable arrangement for scanning the X-ray fan, in accordance with the principles outlined herein, may be employed.

As described hereinbefore, time base generator 28 provides the scanning sawtooth voltage in conventional manner in phase with the sinusoidal voltage provided by synchronous motor power supply 21 and this maintains the desired relationship between lateral scan and rotary motion. The exact relationship obtained is determined by the gearing of motor 9, turning member 6 through a predetermined angle for each cycle of the sinusoidal voltage. Since the sinusoidal voltage is also supplied to pulse forming circuits 17, the integration times are retained in the desired relationship with the scanning of X-ray fan 14 to provide the required effective beam paths.

It has been mentioned that processing, suitable for use with X-ray apparatus of the type described, such as that disclosed in U.S. Pat. No. 3,924,129 operates on data representing the absorption along a plurality of sets of beam paths in the plane of examination, the sets conveniently being sets of parallel paths. The manner in which the present invention provides such data, despite the continuous orbital motion involved will now be described with reference to FIGS. 3 and 4.

FIG. 3 shows in simplified form a scanning arrangement in which the detectors 11 and source anode 13 lie on the same circle, which unlike the example of FIG. 1 is centred on axis 7, and are therefore equidistant from that axis. Thirty four detectors are shown for this simplified arrangement, it being understood that beam paths of radiation incident on those detectors will be represented by their centrelines. The source and detectors are illustrated at what may be considered to be an arbitrary starting position for the scan, at which the source spot of the X-rays is at the extreme right of anode 13 to provide fan 14a as in FIG. 1. Considering now the effect of the orbital motion and lateral motion of the X-ray source spot on anode 13 the relationship between them is arranged to be as shown by the broken lines. In the time in which the spot on anode 13 traverses from extreme right to extreme left of the anode the rotation of rotary member 6 brings anode 13 to the position 13' shown broken so that fan 14b emanates from a point, in relation to a fixed frame of reference such as body 1, which was initially at the centre of anode 13. The identical orbital motion is, of course applied to the detectors 11 taking them to the position of the broken lines so that each detector still intercepts the same beam of the fan 14. It will be observed that the two extreme beams of fan 14, and those intermediate but not shown have moved laterally but remain parallel to their original positions. Thus they are two beam paths of the parallel set of beam paths which this invention provides. In view of the chosen number of integration intervals, in the time of a lateral scan of the X-ray source spot, a further plurality of such parallel beams paths are provided between those shown.

As described hereinbefore the X-ray source spot is then subject to a rapid 'flyback' taking it to the extreme right of the anode at 13' to provide the fan of X-rays shown by the chain dotted line. The X-ray source spot is then at the position which it would have reached in the course of rotation, without the lateral scan, and is therefore inclined. It will be seen however that, while the extreme left hand beam takes a new inclination another beam, in this example the fifth from the left identified by reference numeral 29, takes up a position parallel to those previously taken by the extreme beam. A similar change applies to all other beams in the fan. In the course of the following lateral X-ray spot scan and orbital movement, the fan 14 moves to the position from which fan 14a originated but at the new inclination due to the intervening movement of detectors 11. In that time beam 29 moves to the position of the extreme left hand beam of fan 14a remaining at the same inclination as described hereinbefore. Thus beam 29 provides data for further beam paths of the parallel set started by the extreme left hand beam. In the course of further lateral scans of the X-ray source spot other detectors will contribute data to this, and other, parallel sets extending them, as required, completely across the region including body 1.

It will be observed that at junctions between parts of a parallel set, such as that between the paths examined by beam 29 and those examined by the extreme left hand beam, a path is examined twice by two beams. In practice, because of the finite time of a flyback of the source spot the two beams will not examine exactly the same path thus denying a valuable check between the sensitivities of the different detectors.

In order to provide the overlap, between portions of a parallel set provided by different detectors, which allows such comparisons between detectors, the preferred embodiment of FIG. 1 employs the unequal spacing of source and detectors which is shown in simplified form in FIG. 4.

In that Figure the arrangement has been shown to be substantially identical to that of FIG. 3 except that the source anode 13 and detectors lies on a circle whose centre 7' is displaced from axis 7. The distance between axis 7 and the detector is then twice that between axis 7 and the source, i.e., as shown in FIG. 1. In practice to provide clearance of the body 1 it is likely that the detectors would be moved to twice the radius of a FIG. 3 arrangement. However the difference from FIG. 4 would then merely be one of scale. The scanning motions of the FIG. 4 arrangement are substantially the same as those explained in relation to FIG. 3, the overlap being produced entirely as a result of the geometry adopted. In the course of the initial orbital motion the X-ray source spot is scanned from the extreme right to the extreme left of anode 13 to maintain the beams of fan 14 at the same inclination to the fixed frame of reference, despite the orbital motion, as explained hereinbefore. If the detectors are at the same radius as in FIG. 3 the angular motion to be compensated will be substantially the same. The source anode 13 will now be at half the radius of the anode of FIG. 3 and it will not move through the same distance for the same angular change. Consequently instead of the source spot, scanning to the left hand end of the anode from 13', moving a distance equal to half of the anode length, as in FIG. 3, it now moves a distance equal to two thirds of the anode length, namely to position 30. As before a parallel set of data has been provided by the traverse and orbit combined.

As before the spot 'flies back' to the extreme right of the anode, at 13', giving a new fan, indicated by the wide chain dotted lines and at a new inclination. Also as before one beam, 29 which in this case is the fourth from the left is parallel to the previous positions of the extreme lefthand beam and commences a new portion of the parallel set. However the spot now reaches the end of the anode two thirds of the way along position 13', namely at 30' to provide a beam along path 29' indicated by the fine chain dotted line, to the fourth detector which is displaced as shown. As before flyback follows this to start the next of the series of lateral scanning movements. It will be apparent however that the contributions to the parallel set between the extreme left hand beam paths of 14a and b are overlapped by those between 29 and 29'. Thus the sensitivities of, in this example, the first and fourth detectors on the left can be compared for all beam paths between 29' and the extreme left hand beam of 14a. The same is true for all other detectors of the fan and all other contributions to the parallel sets by further lateral scans of the source spot.

As for the FIG. 3 arrangement finite time flyback will prevent the full attainment of the overlap shown in the Figure but in this example overlap of several beams is still provided. In the course of many lateral source spot scans the arrangement provides that all beam paths, except some at extremes of each parallel set, are examined by two detectors and the detailed geometry may readily be adjusted to provide this despite the finite flyback time. The motion of source and detectors can be described as a rotation about the centre 7' of the circle on which they lie, plus a precession of that centre about axis 7. It will also be understood that, because of this precession of source and detector circle, caused by the off-centre axis, the beam paths described as identical will be different at the extremes of each beam near to the source and detectors. However since they will be substantially identical in the region of the body 1 the conditions required are suitably satisfied. The precession does not otherwise affect the scanning motion.

If required the source may be placed intermediate the positions of FIGS. 3 and 4. It will be apparent that placing the source of FIG. 3 at a slightly reduced distance from axis 7 will give sufficient overlap to negate the effects on that arrangement of the finite flyback time.

It will be seen from the arrangements of FIGS. 3 and 4 that many other arrangements, of source and detector positions, detector numbers fan spread angle etc. may be provided such that the basic principle of the invention is satisfied, namely that the lateral scan of the source spot is sufficient, over a predetermined number of integration intervals, to substantially cancel the orbital motion of the X-ray fan so that the orbital motion is replaced in effect by a lateral displacement.

It should be understood that the arrangement of FIG. 4 is simplified for the purposes of explanation although the relative radii of source and detectors correspond to the preferred embodiment of FIG. 1. The numbers and relative spacing of the detectors in FIG. 4 are not those of the preferred embodiments.

The geometry and the relationships of the two scanning motions of the apparatus are predetermined, although provision may be made to vary them if desired. Consequently the beam paths which will be examined by the detectors in the course of a complete scan are known in advance and are supplied to predetermined locations of a store, in this example a random access memory (RAM) store, in response to the signals, from timing circuits 17, which determine the integration intervals. Each location in the store, representing a beam path may be identified by a suitable co-ordinate system, such as $r$, defined as the distance of the beam path from axis 7 along a perpendicular to the path, and $\theta$, defined as the angle which that perpendicular makes with an arbitrary zero.

The store is indicated schematically at 31 in FIG. 5. The data supplied at 20 on individual circuit paths from log converters 19 are applied to an address selector 32 which, in response to the pulses from circuits 17 supplies them to the appropriate addresses in the predetermined sequence.

Within the box representing store 31 in FIG. 5 there is shown part of a matrix representing storage locations, each appropriate to a beam path and arranged in terms of the appropriate co-ordinates $r$ and $\theta$ for the purposes of illustrating the distribution of data. It will be understood, however, that the data need not, in practice, retain any particular physical distribution in store 31 provided the respective locations are known. For the purposes of illustration five integration intervals have been assumed for each lateral scan of the source spot, instead of the larger number used in practice. In view of the finite flyback time of the source spot a complete overlap is not achieved. The flyback time is, however, arranged to be equal to one integration interval so that the beams of successive parts of a parallel set are displaced by an exact number of beam paths and remain in registration in the parts which do overlap. The data have been identified by the numbers of detectors 11 by which they are derived, the numbering starting at detectors $11_1$ at the extreme left in FIG. 4.

In the course of the first scan of the source spot detector 11, provides data for five beam paths at constant $\theta$ but at increasing $r$, for the co-ordinates chosen, and the data are read by address selector 32 into the appropriate five locations in succession as they are derived. Simultaneously the data for the other detectors are read into locations for other sets at constant $\theta$, displaced from those of $11_1$ as shown. Those for detectors beyond $11_4$ cannot be seen in the part of the storage matrix illustrated in FIG. 5. During the next scan of the source spot, detector $11_4$ provides data for beam paths at the angle $\theta$ appropriate to paths previously examined by $11_1$ but starting at a higher value of $r$. These are also read into their appropriate locations in sequence, as indicated by $11_4'$. It will be seen that two of these locations already contain data for $11_1$. The new data are added to the previous data by any appropriate means, such as recirculation and adding of the previous data. Simultaneously data for the other detectors are read into the locations indicated by the primes. At the next lateral scan of the source spot a further change by three detectors, for a value of $\theta$, is made as shown by $11_7''$ and $11_8''$.

It will be observed that, as a result of the displacement of beam paths provided by the finite flyback time, each beam path will be examined by two detectors, with the exception of some at the end of the scan. In the absence of flyback delay, those beam paths in the region of overlap would have been examined by three detectors. The data for each beam path may merely be combined if desired. Data for these paths being examined only once may be doubled, discarded or their acquisition may be avoided by suitable tailoring of the start and finish of the scan. Alternatively data added into an occupied location may be averaged with those already stored.

The provision of data for two detectors for each beam path allows the reduction of errors due to relative differences of sensitivities of adjacent detectors. Furthermore, since the detectors used change sequentially across a parallel set, differences across a parallel set tend to be smoothed out to the benefit of the finally derived representation. However, as a further refinement the fact that two detectors examine the same path, for which they sould give the same value, allows the possibility of adjusting the gains of their respective amplifiers to equate their sensitivities. Such equalising may be carried right across the bank of detectors 11 by virtue of the successive overlaps.

At the conclusion of the complete scanning motions the store 31 contains data for a plurality of parallel sets of beam paths at different inclinations, as required. These are then suitable for the aforementioned processing and are read out in sequence to a processing computer 33 for processing for example as described in co-pending U.S. Pat. No. 3,924,129.

It has been mentioned that the invention can also be used with an apparatus of the form described in co-pending United States Patent No. 3,946,234 to eliminate the stepping of the orbital motion described in that application. The arrangement described therein employs a fan of radiation of relatively narrower angle together with a mechanical lateral motion of source and detectors to scan the fan across the body to achieve a required number of beam paths. It will be apparent that such a lateral scan, considered in relation to the motion of a single beam of the fan merely imposes a motion at constant $\theta$. Thus the principle of the invention, that the scan of the X-ray source spot temporarily negates the change of $\theta$ imposed by the orbital motion, is not affected by the extra source-and-detector lateral scan. The description of the relationship according to the invention given hereinbefore is therefore still appropriate to this other form of the apparatus although the effects of the superimposed constant $\theta$ motion should be considered when allocating the derived data to their appropriate storage locations.

There is shown in FIG. 6 an example of an apparatus according to the said U.S. Pat. No. 3,946,234 in which features common to the arrangement of FIG. 1 have been indicated by the same reference numerals. The rotary number 6, in this example, carries also two compensating members 34 and 35. These members are arranged to provide a substantially uniform absorption to the radiation for all beam paths of a source detector scan despite the substantially circular cross-section provided by the body 1. Thus it is ensured that any variations of absorption are caused substantially only by variations in the body 1. Such compensating members could also be provided for the FIG. 1 arrangement if desired.

Also secured to the member 6 is a reversible motor 36 which drives a toothed belt 37 by means of a drive shaft 38 journalled in member 6. The belt 37 also passes over an idler wheel 39 also journalled in member 6. Secured to the belt 37 is the source 10, which is of the type described hereinbefore. The source is driven to and fro laterally by the belt 37, being mounted on a bearing travelling in a track 40. A counter balance weight 41 is fixed to the opposite side of belt 37 to compensate for out of balance forces during the lateral movement.

Linked to the source 10 by a light weight but rigid yoke 42 is the collimator/detector unit 12/11. The detectors 11 and collimators 12 also move on a bearing on a track 43 on member 6.

As an alternative to the FIG. 1 arrangement for controlling the relative motions there is provided on turntable 6 a graticule 44 (only shown in part) comprising a translucent strip carrying engraved lines. The lines interrupt a light path between a light source and a photocell in unit 45 to provide pulses indicating the progress of the orbital movement. These pulses are used to cause periodic reversals of motor 36 is accordance with the required relationship. Yoke 19 carries a similar graticule 46 cooperating with light source and photocell unit 47 to provide signals indicative of the progress of the lateral scan of source 10 and detectors 11. These pulses are applied to the integrators 16 to control the integration intervals and to source control/time base generator 28 to control the scan of the source spot along anode 13 in the required relationship. The pulses may also be applied to a counter, not shown, to record the progress of the scan for the purpose of any processing or timing required.

It will be apparent that a photocell graticule combination could also be used to provide timing pulses for the FIG. 1 arrangement in which case pulses from a combination such as 44/45 monitoring the rotary motion would be applied directly to integrators 16 and source control 28.

In a further embodiment of the invention FIG. 7 shows a means for obtaining the required motion of the X-ray beams without the use of a scanning anode X-ray source such as has been described hereinbefore.

In FIG. 7 the detectors 11 are shown in the form of individual scintillator crystals 48 and photomultipliers 49. The X-ray source 10 is in the embodiment a single point source of X-rays incident on the crystals 48. For simplicity only four typical detectors have been shown. A plurality of collimators 50 are provided on a ring 51 which rotates about an axis 52 which is fixed in relation to the source and detectors. In the case of an apparatus such as that shown in FIG. 1 axis 52 is identical with axis 7. However for an apparatus such as that shown in FIG. 6 these are not the same as shown in FIG. 7, since axis 52 moves with the yoke 42.

Each collimator 50, of which only two are shown, is of a width suitable for defining a pencil beam, although in this embodiment each detector is significantly larger. The collimator ring 14 is arranged to rotate in the opposite direction to the rotation of the source and detectors and at such a speed that it matches the orbital motion of the source. Thus while each collimator passes across a detector it remains in a relationship with source 10 such that the pencil beam defined is subject to no rotation but a translational motion is substituted. It will be appreciated that this is the same effect described hereinbefore for the scanning anode source. As the collimator moves to the next detector the following collimator takes its place. Thus there is a sudden angular change corresponding to the flyback of the scanning anode source.

It will be appreciated that the collimators at the opposite side of the ring 51 can pass between the source 10 and the body 1. The ring 51 must, therefore, be slightly inclined in relation to the plane of the slice so that such interference is avoided.

It should further be noted that other collimators which are fixed relative to X-ray source 10 can be provided as close as possible to the body 1 so that as far as possible the body is not subjected to radiation which will not be accepted by collimators 50.

Alternatively collimators 50 may be placed so as to pass between the body and the source instead of between the body and the detectors. In that case the relative motion described would achieve the same effect, however the body would not be subject to radiation which is not to be detected.

What I claim is:

1. An apparatus, for examining the body of a patient by means of penetrating radiation such as x-radiation, the apparatus including: a source of a substantially planar fan-shaped distribution of said radiation; support means arranged to support said source so as to irradiate a slice of said body with said radiation; detector means, including a plurality of detectors arranged to detect the radiation after passage through the body along a plurality of beams at different angles within said distribution; means for angularly moving the support means, and with it the source, about an axis intersecting the slice; and means for repetitively angularly displacing said beams relative to said support means, such that, during each of a series of increments of the angular movement of said support means, each of said beams remains at the same inclination in relation to said body.

2. An apparatus, for examining a body by means of penetrating radiation such as x-radiation, including: source means arranged to irradiate a slice of said body with a fan-shaped distribution of said radiation; a plurality of detectors arranged to detect the radiation after passage through the body along a plurality of beams at different angles within said distribution; scanning means for angularly displacing the source means about an axis intersecting said slice, so as to cause said fan-shaped distribution to assume successively different angular dispositions relative to the body; output means for deriving output signals from said detectors, each detector providing output signals relating to the radiation received thereby along a plurality of beam paths passing through said body in many different positions relative thereto, said scanning means being arranged to produce relative movement between said detectors and said fan-shaped distribution of radiation to cause said output means to derive groups of signals from the detectors, each group representing the radiation received by a respective detector as it views the origin of said fan-shaped distribution in different positions; and means for deriving from the output signals a representation of the variation of absorption in said slice with respect to the penetrating radiation.

3. Radiographic apparatus including: source means arranged to project a fan-shaped distribution of x-rays to irradiate a cross-sectional slice of the body of a patient; a plurality of detectors distributed along an arc and arranged to detect the x-rays after passage through the body along a plurality of beams which are disposed at different angles within said distribution; output means for deriving output signals from said detectors, each output signal relating to x-radiation received by a respective detector along a beam path passing through the body; scanning means for angularly displacing the source means about an axis intersecting said slice, to angularly displace the fan-shaped distribution relative to the body, and providing relative movement between the fan-shaped distribution and the detectors, to cause each detector to view the origin of the radiation in a succession of different positions and the output means to derive from each detector groups of output signals, each group representing the x-radiation received by a respective detector along paths originating at said different positions; and means for deriving from the output signals a representation of the variation of absorption of the x-rays with position in said slice.

4. An apparatus, for examining a body by means of penetrating radiation, such as X-radiation, including: source means arranged to irradiate a slice of the body with a spread of the radiation, a plurality of detectors including detectors arranged to detect the radiation after passage through the body along a plurality of beams angularly distributed in the spread, means for deriving from the detectors, output signals indicative of the amount of absorption of the radiation along paths traversed by the respective beams through the slice, means for displacing the beams of radiation to direct them along different paths through the body such that each beam traverses at different times, several paths of each of a plurality of sets of parallel paths in the slice and such that, for each such set, regions of the slice defined by the paths traversed by respective beams each overlap, at least in part, at least one region defined by substantially parallel paths traversed by another beam.

5. An apparatus, for examining a body by means of penetrating radiation such as X-radiation, including source means arranged to irradiate substantially the whole of a region of interest in a slice of said body with a spread of the radiation, a plurality of detectors including detectors arranged to detect the radiation after passage through the body along a plurality of beams angularly distributed in the spread, means for deriving from the detectors output signals indicative of the radiation detected thereby along the paths traversed by the said beams through the slice, means for angularly displacing the beams of radiation to direct them along different paths angularly distributed in the slice to cause the detectors to provide further output signals relating to those different paths, means for additionally subjecting the beams of radiation to further displacements to displace each beam partly across the region of interest, to cause each detector to provide subsets of output signals each relating to a plurality of parallel paths in the said slice, means for combining subsets of output signals provided by different detectors corresponding to paths, all of which are substantially parallel, to provide sets of output signals relating to parallel paths distributed across substantially the whole of said region, and means for processing the said sets of output signals to provide a representation of the distribution of the absorption of the radiation in the said slice.

6. An apparatus, for examining a body by means of penetrating radiation such as x-radiation, including: source means arranged to irradiate a slice of said body with a fan shaped distribution of said radiation; a plurality of detectors arranged to detect the radiation after passage through the body along a plurality of beams at different angles within said distribution; means for angularly displacing the source means about an axis intersecting said slice; means for additionally subjecting the beams of radiation to a repetitive additional displacement, substantially equal and opposite to that resulting from the angular displacemnt of the source means, so that each of said beams remains, throughout each repetition of the additional angular displacement, substantially parallel to its position at the start thereof and so that each detector receives radiation along at least some paths previously examined by another detector; and means for providing a single absorption value for each beam path examined by more than one detector despite differences in the sensitivities of the detectors.

7. An apparatus according to claim 6 in which said means for providing a single absorption value comprises means for combining the output signals of said different detectors.

8. An apparatus, for examining a body by means of penetrating radiation such as x-radiation, including: source means arranged to irradiate a slice of said body with a fan-shaped distribution of said radiation; a plurality of detectors arranged to detect the radiation after passage through the body along a plurality of beams at different angles within said distribution: means for angularly displacing the source means about an axis intersecting said slice; and means for additionally subjecting the beams of radiation to a repetitive additional angular displacement, substantially equal and opposite to that resulting from the angular displacement of the source means, so that each of said beams remains, throughout each repetition of the additional angular displacement, substantially parallel to its position at the start thereof, wherein absorption values for at least some beam paths are provided by the combination of output signals relating to a plurality of substantially parallel paths.

9. An apparatus according to claim 8 wherein the said substantially parallel paths, of which output signals are combined, are substantially coincident.

10. An apparatus, for examining a body by means of penetrating radiation, such as X-radiation, including: source means arranged to irradiate a slice of the body with a spread of the radiation originating substantially from a point, a plurality of detectors including detectors arranged to detect the radiation after passage through the body along a plurality of beams angularly distributed in the spread, means for deriving, from the detectors, output signals indicative of the amount of absorption of the radiation along paths traversed by the respective beams, means for angularly displacing the source means and detectors about an axis intersecting the said slice, and means for additionally and periodically displacing the point of origin of the radiation to cause each beam of the spread, during each period of the additional displacement, to traverse the body along a plurality of paths defining a linear zone in said slice, the arrangement being such that each zone defined by paths traversed by one beam overlaps, at least in part, at least one other zone defined by paths traversed by a different beam from substantially the same mean direction.

11. An apparatus according to claim 10 in which the first mentioned displacement is a continuous angular displacement and the means providing the additional displacement comprises means for laterally displacing the point of oringin of the radiation in a direction substantially perpendicular to the mean direction of propagation of the radiation.

12. An apparatus according to claim 10 in which said source means is an X-ray source including an elongated anode, arranged to provide X-rays in response to electrons incident thereon, and means for displacing the point of incidence on said anode to displace said X-rays in relation to said body to provide said additional displacement.

13. An apparatus according to claim 10 wherein said source means is disposed closer to said axis than said detectors.

14. An apparatus according to claim 13 wherein the distance between said source means and said axis is substantially half of the distance between said detectors and said axis.

15. An apparatus according to claim 10 wherein absorption values for at least some beam paths are provided by the combination of output signals relating to a plurality of substantially parallel paths.

16. An apparatus according to claim 15 wherein the said substantially parallel paths, of which the output signals are combined, are substantially coincident.

17. An apparatus according to claim 10 wherein the two said displacements are arranged to cause each detector to receive radiation along at least some paths previously examined by another detector.

18. An apparatus according to claim 17 including means for providing a single absorption value for each beam path examined by more than one detector despite differences in the sensitivities of the detectors.

19. An apparatus according to claim 18 in which said means for providing a single absorption value comprises means for combining the output signals of said different detectors.

20. An apparatus for examining the body of a patient, by means of penetrating radiation such as X-radiation, including:

means defining a patient position and source means disposed outside the patient position to generate penetrating radiation and to project said radiation along a fan-shaped swath, of sufficient extent to irradiat a region of interest of the body, within a slice intersecting the patient position;

means for detecting the radiation after emergence from the patient position, said detecting means comprising a plurality of detector devices receiving the radiation along respective beams, angularly distributed within the fan-shaped swath, and means for deriving, from the detector devices, respective signals each indicative of absorption suffered by the radiation in passing through the patient position along the path of the respective beam;

means for angularly displacing the source means and detecting means about an axis intersecting the said slice to project the fan-shaped spread of radiation through the patient position from a plurality of mean directions;

means for additionally displacing the said swath within the said slice to cause each beam to follow in succession a series of paths which are parallel to one another and to provide signals therefor, the extent of said additional displacement being small in relation of the extent of said region of interest;

means for combining the signal provided by each detector for a group of such parallel paths with those provided by other detectors at other times for further groups of paths which are parallel to the first mentioned group, to provide sets of signals each relating to a larger group of parallel paths of sufficient extent to include the entire region of interest of the body of a patient in said patient position, and means for processing the said sets of signals to provide the absorption coefficient, with respect to the penetrating radiation, at each of a plurality of elemental locations distributed over said slice.

21. An apparatus according to claim 20 wherein the means for displacing are arranged so that the individual groups of parallel paths forming each further group each define regions of the said slice which overlap one another at least in part.

22. An apparatus according to claim 20 in which the first mentioned displacement is a continuous angular displacement and the means providing the additional displacement comprises means for laterally displacing the point of origin of the radiation in a direction substantially perpendicular to the mean direction of propagation of the radiation.

23. An apparatus according to claim 20 in which the first mentioned displacement is an intermittent angular displacement and the means providing the additional displacement comprises means for laterally displacing the point of origin of the radiation, in a direction substantially perpendicular to the mean direction of propagation of the radiation, during pauses in said intermittent displacement.

24. An apparatus according to claim 20 wherein the two said displacements are arranged to cause each detector to receive radiation along at least some paths previously examined by another detector.

25. An apparatus according to claim 24 including means for providing a single absorption value for each beam path examined by more than one detector despite differences in the sensitivities of the detectors.

26. An apparatus according to claim 25 in which said means for providing a single absorption value comprises means for combining the output signals of said different detectors.

27. An apparatus according to claim 20 wherein absorption values for at least some beam paths are provided by the combination of output signals relating to a plurality of substantially parallel paths.

28. An apparatus according to claim 27 wherein the said substantially parallel paths, of which the output signals are combined, are substantially coincident.

* * * * *